US009500763B2

(12) United States Patent
Vigneaux

(10) Patent No.: US 9,500,763 B2
(45) Date of Patent: Nov. 22, 2016

(54) DOWNHOLE FLUID COMPOSITION SENSING

(71) Applicant: Schlumberger Technology Corporation, Sugar land, TX (US)

(72) Inventor: Pierre Vigneaux, Moisenay (FR)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/800,630

(22) Filed: Jul. 15, 2015

(65) Prior Publication Data
US 2016/0018554 A1    Jan. 21, 2016

(30) Foreign Application Priority Data

Jul. 18, 2014  (EP) ..................................... 14290214

(51) Int. Cl.
| | | |
|---|---|---|
| *G01V 5/04* | (2006.01) | |
| *G01V 3/30* | (2006.01) | |
| *G01V 8/00* | (2006.01) | |
| *G01N 21/31* | (2006.01) | |
| *G01N 21/15* | (2006.01) | |
| *E21B 49/08* | (2006.01) | |

(52) U.S. Cl.
CPC ............... *G01V 3/30* (2013.01); *E21B 49/088* (2013.01); *G01N 21/15* (2013.01); *G01N 21/31* (2013.01); *G01V 8/00* (2013.01); *E21B 2049/085* (2013.01); *G01N 2021/152* (2013.01); *G01N 2201/0693* (2013.01); *G01N 2201/0696* (2013.01)

(58) Field of Classification Search
CPC ...................................................... G01V 5/102
See application file for complete search history.

(56) References Cited

U.S. PATENT DOCUMENTS

| | | | |
|---|---|---|---|
| 6,394,182 B1 * | 5/2002 | Fadel | 166/265 |
| 2002/0043620 A1 * | 4/2002 | Tchakarov et al. | 250/269.1 |
| 2003/0048450 A1 | 3/2003 | Pope et al. | |
| 2004/0232340 A1 | 11/2004 | Benson | |
| 2005/0269499 A1 | 12/2005 | Jones et al. | |
| 2007/0035737 A1 | 2/2007 | Andrews et al. | |
| 2008/0165356 A1 | 7/2008 | DiFoggio et al. | |
| 2013/0334412 A1 | 12/2013 | Gunn et al. | |

\* cited by examiner

*Primary Examiner* — David Porta
*Assistant Examiner* — Hugh H Maupin
(74) *Attorney, Agent, or Firm* — Michael Dae

(57) ABSTRACT

The present disclosure introduces a downhole tool conveyable within a tubular within a wellbore extending into a subterranean formation. The downhole tool includes a body and a member having a first end and a second end, wherein the first end is rotatably coupled to the body. A spectrometry sensor is disposed proximate the second end of the member. Embodiments also include a fluid separating component shaped such that a heavier fluid from the fluid flowing along the downhole tool is drawn away from the spectrometry window to reduce window contamination from fluid droplets, particles, and/or liquids.

18 Claims, 12 Drawing Sheets

DOWNHOLE FLUID COMPOSITION SENSING

CROSS REFERENCE TO RELATED APPLICATIONS

This application claims the benefit of priority to European Patent Application 14290214.7, filed on Jul. 18, 2014, the entire content of which is incorporated herein by reference.

BACKGROUND OF THE DISCLOSURE

In the oil and gas industry, production logging is utilized to determine the gas and water phases of a multi-phase production flow, such as to develop production and/or remedial strategies. However, in lateral wells or well portions that are substantially horizontal, the heaviest phase (e.g., water in a water-oil-gas flow) segregates towards the bottom of the production tubing, and the lightest phase (e.g., gas in a water-oil-gas flow) segregates towards the top of the production tubing. Such gravity-induced segregation creates challenges when operating production-logging tools to determine composition of the gas phase, because the sensors of such production-logging tools may not be located within the cross-sectional portion of the production tubing that substantially contains the gas phase. For example, when the measurement region surrounding the sensors is substantially occupied by liquid, the resulting data is useless and discarded.

Such sensors also include an optical window serving to isolate the production flow from the actual sensing element of the sensor. However, oil from the production flow may foul the optical window. Such fouling can also adversely affect sensor data, and perhaps render the sensor functionally blind.

SUMMARY OF THE DISCLOSURE

The present disclosure introduces an apparatus that includes a downhole tool conveyable within a tubular within a wellbore extending into a subterranean formation. The downhole tool includes a body and a member having a first end and a second end. The first end is rotatably coupled to the body. A spectrometry sensor is disposed proximate the second end of the member.

The present disclosure also introduces an apparatus that includes a downhole tool conveyable within a tubular within a wellbore extending into a subterranean formation. The downhole tool includes a body, an optical sensor operable in the detection of a compositional component of a fluid in the tubular, and a member operable to position the optical sensor away from the body.

The present disclosure also introduces a method that includes conveying a downhole tool within tubular within a wellbore extending into a subterranean formation. The downhole tool includes a member having a first end rotatably coupled to a body, as well as a spectrometry sensor disposed proximate a second end of the member. The spectrometry sensor is positioned in a gaseous portion of a multiphase fluid flowing within the tubular by rotating the member away from the body.

The present disclosure also introduces an apparatus having a downhole tool that is conveyable in a tubular in a wellbore extending into a subterranean formation. The downhole tool includes a body and a spectrometry sensor on the body. A spectrometry window substantially covers the spectrometry sensor from an outside of the downhole tool, separating the sensor from contacting the subterranean formation. The downhole tool also includes a fluid separating component configured about the body. The fluid separating component is shaped such that a heavier fluid from a fluid flow along the downhole tool is drawn away from the spectrometry window. The heavier fluid includes components of fluid that is heavier than dry gas, and may include, for example, droplets, particles, liquids, or combinations thereof.

Additional aspects of the present disclosure are set forth in the description that follows, and/or may be learned by a person having ordinary skill in the art by reading the materials herein and/or practicing the principles described herein. At least some aspects of the present disclosure may be achieved via means recited in the attached claims.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
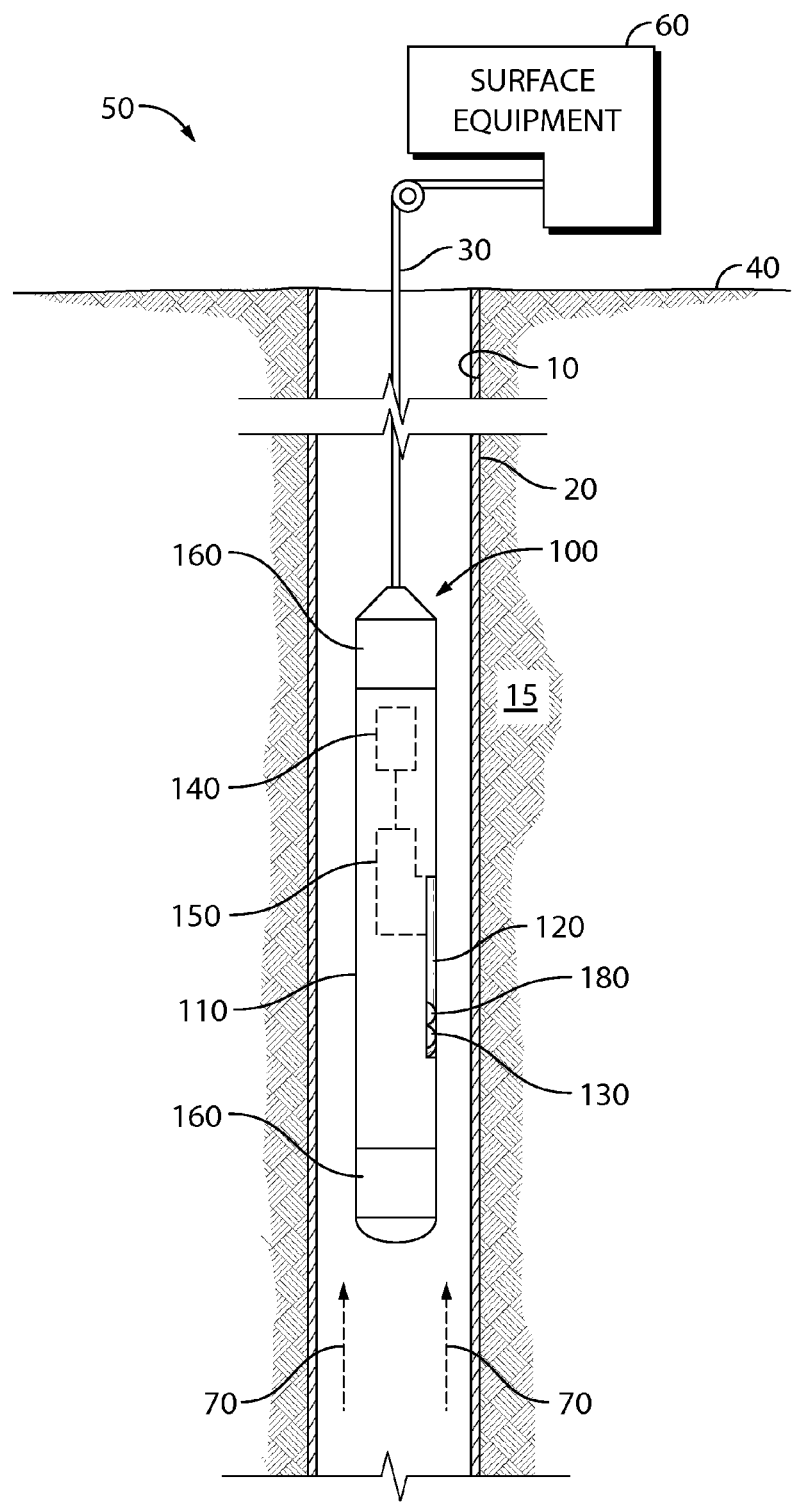
FIG. 1 is a schematic view of at least a portion of apparatus according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting.

In addition, the present disclosure may repeat reference numerals and/or letters in the various examples. This repetition is for simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

FIG. 1 is a schematic view of at least a portion of a downhole tool 100 that may be utilized to determine the composition of a gas phase of a multiphase production fluid flowing within the production tubing 20 of a wellbore 10 according to one or more aspects of the present disclosure. The wellbore 10 extends from the surface 40 of a wellsite 50 to a subterranean formation 15. The downhole tool 100 is conveyable within the production tubing 20 by a multi-conductor cable 30 that is spooled on a winch (not shown) at the surface 40 of a wellsite 50 associated with the wellbore 10. Although not illustrated as such, the downhole tool 100 may form a portion of a tool string conveyed in the wellbore 10 via the multi-conductor cable 30. At the surface 40, the cable 30 is communicatively coupled to an electrical control and data acquisition system and/or other surface equipment, as generally designated in FIG. 1 by reference numeral 60.

FIG. 1 also depicts the downhole tool 100 as being utilized in a production-logging implementation, in which the production tubing 20 lines or is otherwise installed in the wellbore 10. For example, in the example implementation shown in FIG. 1, a multi-phase production fluid is flowing towards the surface 40 in an uphole direction, as indicated by arrow 70 (and more clearly depicted in FIG. 2). However, one or more aspects of the present disclosure may be applicable or readily adaptable to other implementations, such as may be utilized in determining composition and/or other parameters of fluid flowing in an open or uncased wellbore, a pipeline, and/or another fluid flow channel or conduit.

The downhole tool 100 may comprise various combinations and/or arrangements of a body 110, a sensor member 120, an electronics module 140, and an actuator 150. The sensor member 120 carries at least one of a spectrometry sensor 130 and a light source 180. The sensor member 120 and spectrometry sensor 130 are depicted in FIG. 1 as being in a retracted position relative to the body 110.

Figure 2:
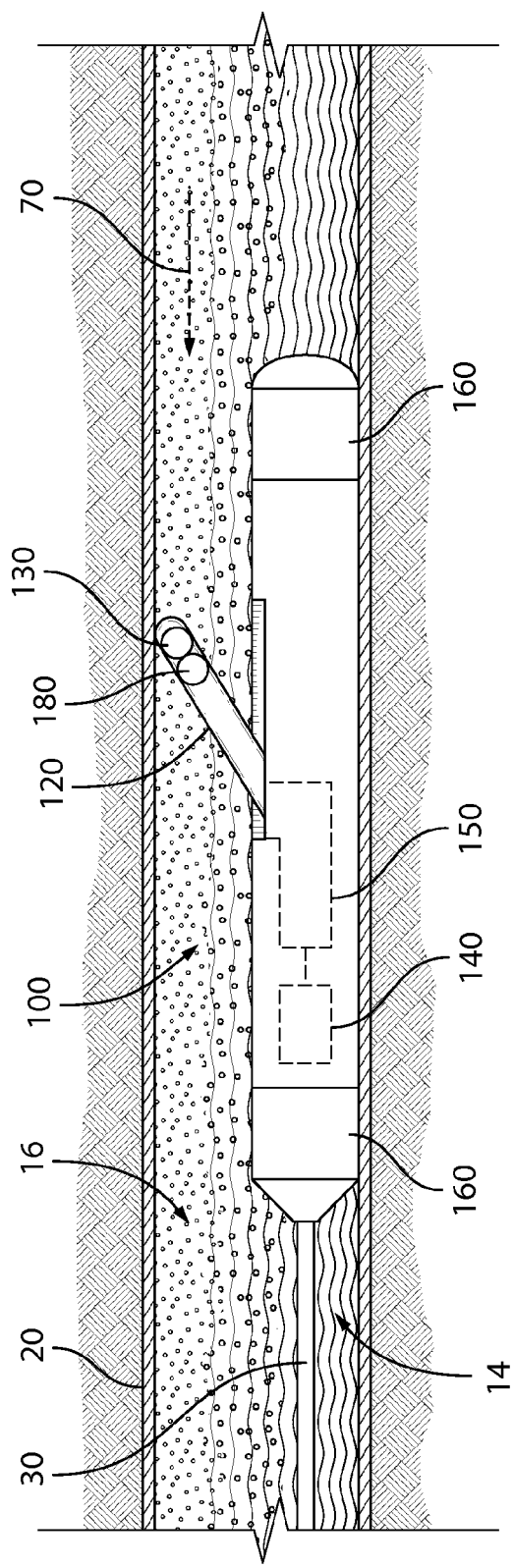
FIG. 2 is a schematic view of an example implementation of the apparatus shown in FIG. 1 according to one or more aspects of the present disclosure.

FIG. 2 is a schematic view of the downhole tool 100 shown in FIG. 1, in which the downhole tool 100 is positioned in a substantially horizontal or otherwise deviated portion of the wellbore 10, and the sensor member 120, the spectrometry sensor 130, and the light source 180 are deployed away from the body 110 via operation of the actuator 150. For example, the actuator 150 may be operable to rotate the sensor member 120 away from the body 110, such that the body 110 may settle towards a lower cross-sectional portion 14 of the wellbore 10 where the gas holdup is lower, and the spectrometry sensor 130 may simultaneously be positioned towards and/or in an upper cross-sectional portion 16 of the wellbore 10 where the gas holdup is higher. Such deployment may be operable to position the spectrometry sensor 130 in the cross-sectional portion having the highest gas holdup at the current depth/station within the wellbore 10 (i.e., in the upper portion 16).

As also shown in FIGS. 1 and 2, the downhole tool 100 may comprise one or more swivels 160 facilitating rotation of the downhole tool 100 within the wellbore 10. The one or more swivels 160 may be or comprise conventional or future-developed devices permitting rotation of at least a portion of the downhole tool 100 relative to another portion of the downhole tool 100, the production tubing 20, and/or the multi-conductor cable 30. The one or more swivels 160 may have a limited range of rotation, such as about 720 degrees and/or another range that may aid in avoiding mechanical damage to electrical and/or hydraulic members extending through each swivel 160. In other implementations, the range of rotation may not be limited, and the swivel 160 may provide an electrical and/or hydraulic connection between opposing sides, in additional to the mechanical connection.

Figure 3:
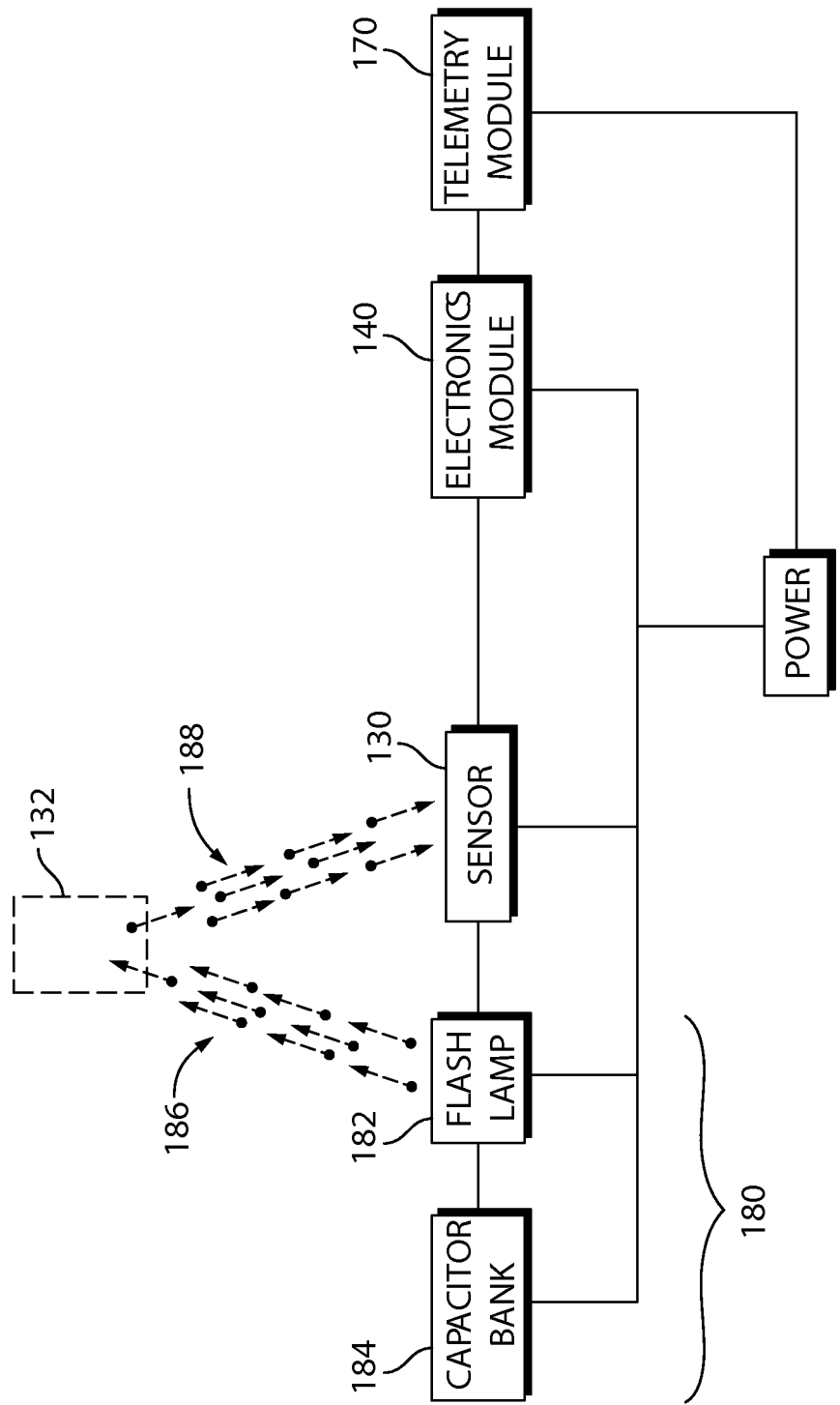
FIG. 3 is a block-diagram of at least a portion of an example implementation of the apparatus shown in FIG. 1 according to one or more aspects of the present disclosure.

FIG. 3 is a box diagram of at least a portion of an example implementation of the electronics module 140, the spectrometry sensor 130, the light source 180, and/or other electronic components of the downhole tool 100 shown in FIGS. 1 and 2. The downhole tool 100 may comprise a telemetry module 170 providing an interface for data and control signals between the surface equipment 60 and the electronics module 140 and/or other portions of the downhole tool 100.

The light source 180 is operable in conjunction with the spectrometry sensor 130. For example, the light source may comprise a flash lamp 182 driven by electrical power received from the surface equipment 60 and/or one or more capacitors, referred to herein as a capacitor bank 184. The light source 180 may be located adjacent or proximate the spectrometry sensor 130, including implementations in which the spectrometry sensor 130 includes the light source 180, or the light source 180 may be or comprise one or more discrete components located remote from the spectrometry sensor 130 (such as within the electronics module 140 and/or another location within the body 110), in which case one or more optical conductors (not shown) may extend from the light source 180 and terminate adjacent or proximate the spectrometry sensor 130 near the end of the sensor member 120.

Similarly, the spectrometry sensor 130 carried with the sensor member 120 may be or comprise an end of one or more optical conductors (not shown) extending from the sensor member 120 to a spectrometry device (not shown) within the electronics module 140 and/or another location within the body 110. Thus, light may be transmitted from within the body 110 to the sensor member 120 by one or more optical conductors, and the backscattered light coming from the illuminated sample may be collected either by the same one or more optical conductors or by another one or more optical conductors and directed towards the spectrometry device located in the body 110.

Accordingly, reference herein to the light source 180 carried with the sensor member 120 may include at least one optical conductor end, terminal, or other termination carried with the sensor member 120, wherein the at least one optical conductor transmits light from one or more light emitting components located within the body 110 to the end(s), terminal(s), or other termination(s) carried by the sensor member 120, thus illuminating fluid in the upper cross-sectional portion 16 of the wellbore 10. In a similar manner, reference herein to the spectrometry sensor 130 carried with the sensor member 120 may include at least one optical conductor end, terminal, or other termination carried with the sensor member 120, wherein the at least one optical conductor transmits backscattered light from the illuminated fluid in the upper cross-sectional portion 16 of the wellbore 10 from the end(s), terminal(s), or other termination(s)

carried by the sensor member 120 to one or more spectroscopy components located within the body 110. Moreover, at least one of the one or more "illuminating" optical conductors (i.e., those transmitting light from the one or more light emitting components located within the body 110 to the end(s), terminal(s), or other termination(s) thereof to illuminate the fluid in the upper cross-sectional portion 16 of the wellbore 10) may also be at least one of the one or more "detecting" optical conductors (i.e., those transmitting light backscattered by the fluid in the upper cross-sectional portion 16 of the wellbore 10 from the end(s), terminal(s), or other termination(s) to the one or more spectrometry sensors located within the body 110).

FIG. 3 also depicts a power source 190 providing electrical power to various components. The power source 190 may be or comprise one or more batteries carried with the downhole tool. The power source 190 may also or instead comprise or be implemented as surface equipment operable to transmit electric power to the downhole tool via the conveyance means 30, such as the surface equipment 60 shown in FIG. 1, among other possibilities within the scope of the present disclosure.

With reference to FIGS. 2 and 3, collectively, the light source 180 may be operable to emit photons 186 into the upper cross-sectional portion 16 of the wellbore 10 where the gas holdup is higher relative to the remainder of the multi-phase fluid flow 70. This causes photons 188 to be emitted at wavelengths corresponding to compositional components of the gas. The spectrometry sensor 130 detects the emitted photons 188 and outputs a corresponding multi-channel signal. For example, the spectrometry sensor 130 may be or comprise a six-channel sensor, with one channel corresponding to each of C1 (methane), C2 (ethane), C3-5 (propane, butane, and pentane), C6+(hexane and higher), CO2 (carbon dioxide), and H2S (hydrogen sulfide). However, the spectrometry sensor 130 is not limited to this one example, and may include a different number of channels each corresponding to different and/or additional compositional components. For example, the spectrometry sensor 130 may be or comprise a thirteen-channel sensor, with one channel corresponding to each of C1, C2, C3, C4, C5, C6, C7 (heptane), C8 (octane), C9 (nonane), C10 (decane), CO2, H2S, and N2 (nitrogen).

The photon data at each wavelength range/channel is communicated to the electronics module 140, such as via one or more electrical and/or optical conductors (not shown). The electronics module 140 may convert the photon data into digital data and/or send the raw photon and/or digitized data to the telemetry module 170 and/or a surface data acquisition system, such as may be included in the surface equipment 60 shown in FIG. 1.

The light source 180 may transmit photons in the manner described above to a measurement region 132 located in the fluid flow 70 adjacent the spectrometry sensor 130. A volume of the measurement region 132 may be less than about five cubic millimeters, such as about one cubic millimeter. However, the measurement region 132 may also have other dimensions within the scope of the present disclosure. The measurement region 132 may also be split into several sub-regions (not shown) that may or may not be co-located. For example, such implementations may aid in avoiding concentrating too much power in one location, such as to prevent damaging the optical pressure barrier and/or the fluid sample being analyzed.

Figure 4:
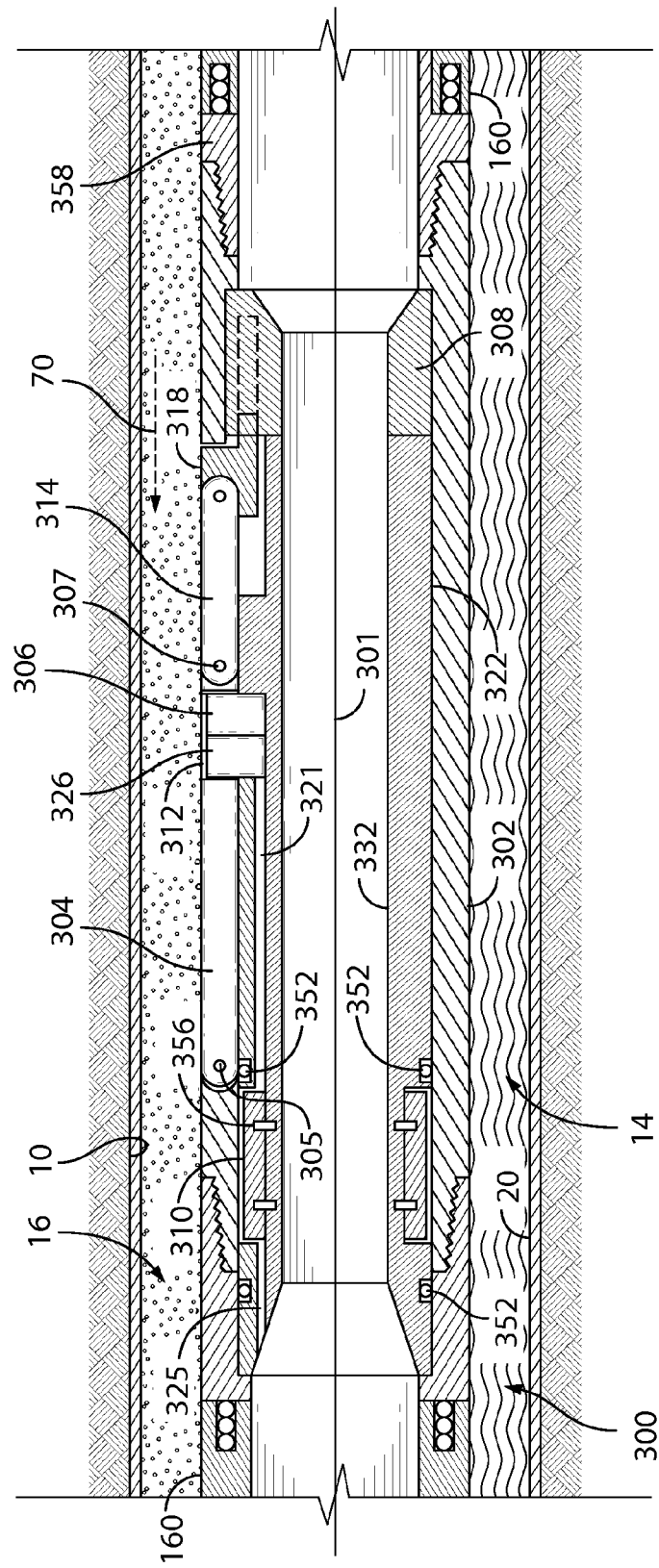
FIG. 4 is a sectional view of at least a portion of an example implementation of the apparatus shown in FIG. 1 according to one or more aspects of the present disclosure.
Figure 5:
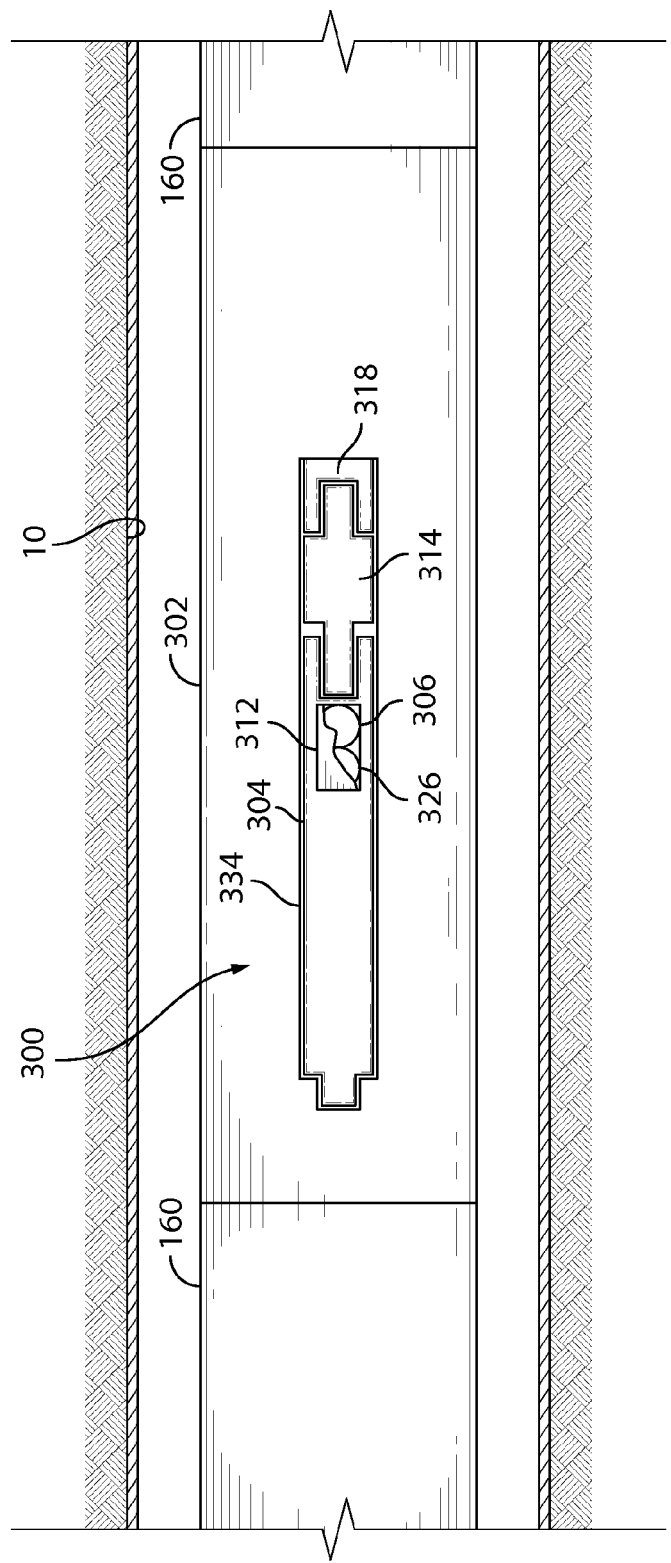
FIG. 5 is a plan view of the apparatus shown in FIG. 4.

FIG. 4 is a sectional view of an example implementation of the downhole tool 100 shown in FIGS. 1-3, designated hereinafter by reference numeral 300. FIG. 5 is a top or plan view of the downhole tool 300 shown in FIG. 4 (the fluid flow 70 depicted in FIG. 4 is omitted from FIG. 5 for clarity). The downhole tool 300 shown in FIGS. 4 and 5 may be substantially similar to the downhole tool 100 shown in FIGS. 1-3, with the following possible exceptions, although the following exceptions may also be applicable or readily adaptable to the apparatus shown in one or more of FIGS. 1-3.

The downhole tool 300 includes a body 302 that may have threaded connectors 358 at one or both ends. The threaded connectors 380 may be or comprise an interface to other components conveyed in the wellbore 10 with the downhole tool 300, such as the swivels 160 described above and/or other downhole tools. Other connections may be utilized instead of or in addition to the threaded connections 358. The body 302 may be substantially similar to the body 110 described above, with the following possible exceptions.

A sensor member 304 is connected to the body 302 by a pin and/or other connector 305 on one end, and is connected to a positioning member 314 by a pin and/or other connector 307 on the other end. The positioning member 314 is attached to an actuator arm 318 by a pin and/or other connector 309.

An electric, hydraulic, and/or other type of actuator 308 is operable to impart movement to the actuator arm 318, such as in a linear direction substantially parallel with the longitudinal axis 301 of the downhole tool 300. The actuator 308 may also be or comprise one or more compression springs and/or other biasing devices operable to open the sensor member 304 to its maximum possible aperture within the well. The sensor member 304 may optionally be maintained in a retracted position via operation of an electric or electromagnetic mechanism, such as may avoid premature opening and/or mechanical wear. Such mechanism may be remotely actuated, such that the sensor member 304 may be deployed upon the request of a human operator.

The movement of the actuator arm 318 may impart motion to the positioning member 314 via the connector 309, and then to the sensor member 304 via the connectors 307 and 305, due in part to the sensor member 304 being pivotably anchored to the body 302 by the connector 305. Thus, the sensor member 304 and the positioning member 314 may each rotate and/or otherwise extend away from the body 302, perhaps in opposite rotational directions, as depicted in FIG. 6.

Figure 6:
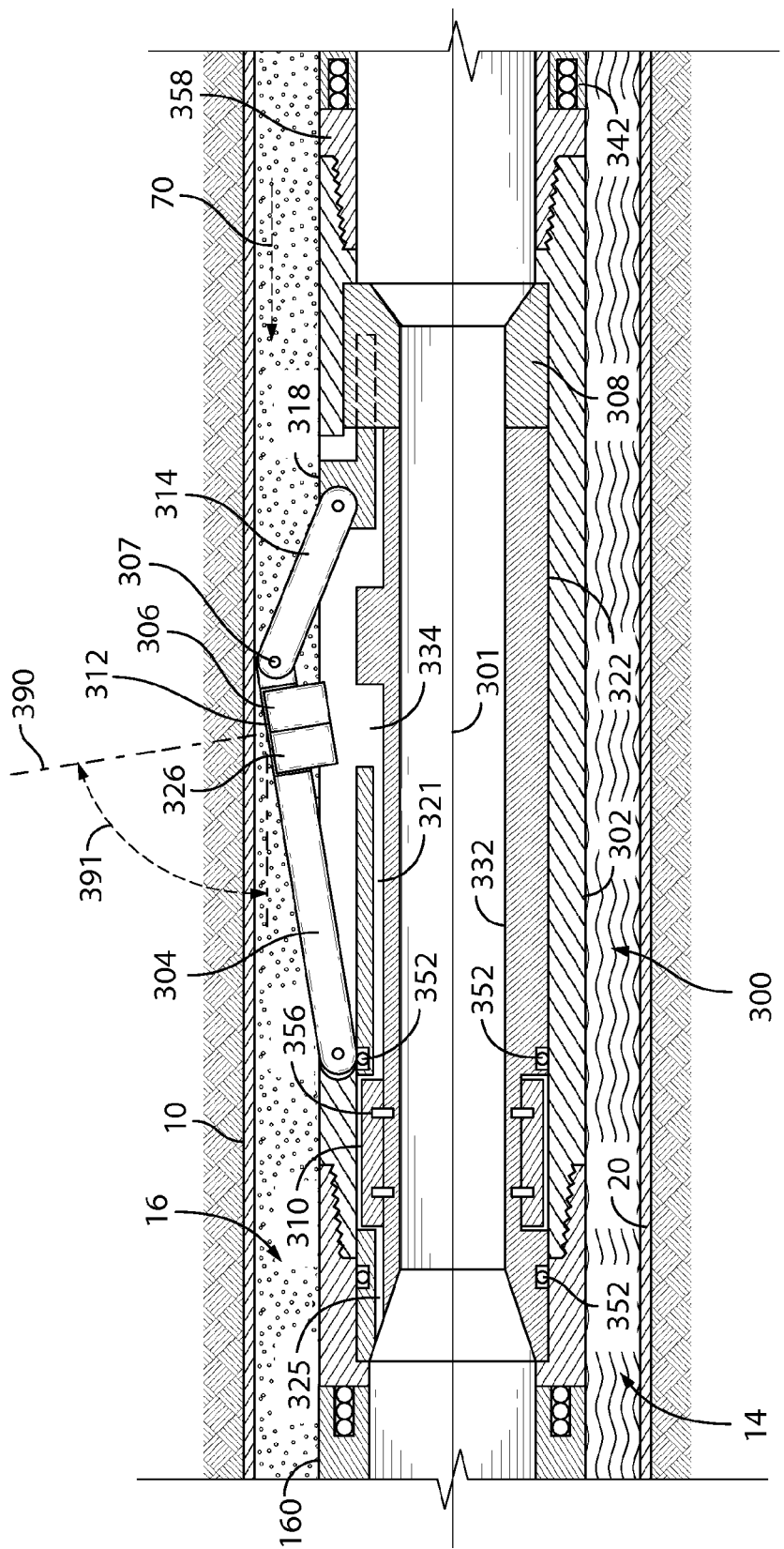
FIG. 6 is a sectional view of the apparatus shown in FIG. 4.

Referring to FIGS. 4-6, collectively, the sensor member 304 includes or otherwise carries a spectrometry sensor 306 at or near the end proximate the connector 307. The spectrometry sensor 306 may be substantially similar to the spectrometry sensor 130 described above. The spectrometry sensor 306 includes or is otherwise associated with a light source 326 and an optical window 312. The light source 326 may be substantially similar to the light source 180 shown in one or more of FIGS. 1-3. The optical window 312 may isolate the spectrometry sensor 306 and/or the light source 326 from the production fluid flow 70, and/or may otherwise protect the spectrometry sensor 306 and/or the light source 326 from damage and/or contamination. The optical window 312 may extend over both the spectrometry sensor 306 and the light source 326, as shown in FIGS. 4-6, or may include two elements, each covering or otherwise corresponding to one of the spectrometry sensor 306 and the light source 326. The optical window 312 may substantially comprise sapphire and/or other materials that are substantially optically transparent.

When the sensor member 304 is in the retracted position shown in FIGS. 4 and 5, the optical window 312 may face radially outward from the body 302, and may be substantially flush with and/or recessed within the outer circumference of the body 302 and/or other portions of the downhole tool 300. For example, one or more of the sensor member 304, the positioning member 314, the spectrometry sensor 306, and the light source 326 may be received in a recess 334 in an outer surface of the body 302. The recess 334 may also extend radially inward into an inner sleeve 322.

The downhole tool 300 may also comprise an electronics module 310 electrically connected to the spectrometry sensor 306 and the light source 326 by one or more electrical and/or optical conductors (not shown) routed along the sensor member 304 and/or through a conduit 321 in the inner sleeve 322. Another conduit 325 on the uphole end of the inner sleeve 322 may be utilized to provide communication between the electronics module 310 and surface equipment or a telemetry system in communication with the surface equipment (such as the surface equipment 60 shown in FIG. 1). The electronics module 310 may be physically coupled to the sleeve 322 by one or more screws, pins, and/or other types of fasteners 356, although the electronics module 310 may instead be physically coupled to or carried by a component of the downhole tool 300 other than the inner sleeve 322. Seals 352 may isolate the electronics module 310 from downhole fluids. The inner sleeve 322 and other portions of the downhole tool 300 may also have a central passageway 332 permitting the passage of fluid flow and/or other downhole tools. The inner sleeve 322 may be a discrete component, as depicted in FIGS. 4 and 6, or instead may be integral to the body 302 and/or other portion of the downhole tool 300.

The electronics module 310 may provide power to the light source 326. However, the light source 326 may merely be an optical output operable to emit light received from the electronics module 310 and/or another component of the downhole tool 300 that is operable to generate and transmit light to the light source 326, such as by one or more optical conductors (not shown). The electronics module 310 may also be operable to send control signals to the spectrometry sensor 306 and/or the light source 326, and perhaps other components of the downhole tool 300. The electronics module 310 may also be operable to receive data signals from the spectrometry sensor 306 and/or other components of the downhole tool 300.

As shown in FIGS. 4 and 6 and described above, the actuator 308 may be operable to move the actuator arm 318 in a linear direction to rotate and/or otherwise extend the sensor member 304 away from the body 302. For example, the actuator 308 and the actuator arm 318 may be threadedly coupled, such that rotational motion of the actuator 308 imparts linear motion to the actuator arm 318. The sensor member 304 and the positioning member 314 may thus be cooperatively extended from the body 302 to position the spectrometry sensor 306 and/or the optical window 312 in the gaseous portion of the production fluid flow (e.g., in the upper cross-sectional region 16 shown in FIG. 2). Such positioning may include orienting the outer face of the spectrometry sensor 306 and/or the optical window 312 such that a normal vector 390 extending perpendicular from the outer face is angularly offset from the direction of production fluid flow 70 by an angle 391, which may not be greater than about ninety degrees. In other implementations, the angle 391 may be greater than about ninety degrees. However, the likelihood of the spectrometry sensor 306 and/or the optical window 312 becoming fouled may substantially increase in implementations in which the angle 391 exceeds ninety degrees and approaches 180 degrees.

As with the implementation depicted in FIG. 2, the downhole tool 300 may comprise and/or be coupled between opposing swivels 160, such that the downhole tool 300 may rotate around the longitudinal axis 301 in response to extension and/or rotation of the sensor member 304 and/or the actuator member 314 away from the body 302. Thus, for example, as the actuator 308 and/or other components operate to rotate and/or extend the sensor member 304 away from the body 302, an end of the sensor member 304 and/or the actuator member 314 will contact the production tubing 20, and the swivels 160 will then permit rotation of the downhole tool 300 relative to the production tubing 20 so that the spectrometry sensor 306 and/or the optical window 312 will be positioned at or near the top of the wellbore 10 (e.g., in the upper cross-sectional region 16) while the body 302 of the downhole tool 300 is simultaneously positioned at or near the bottom of the wellbore 10, which may be aided by gravitational forces. After sufficient data has been obtained via the spectrometry sensor 306, operation of the actuator 308 may retract the sensor member 304 back towards the body 302 and, if provided, into the recess 334.

Figure 7:
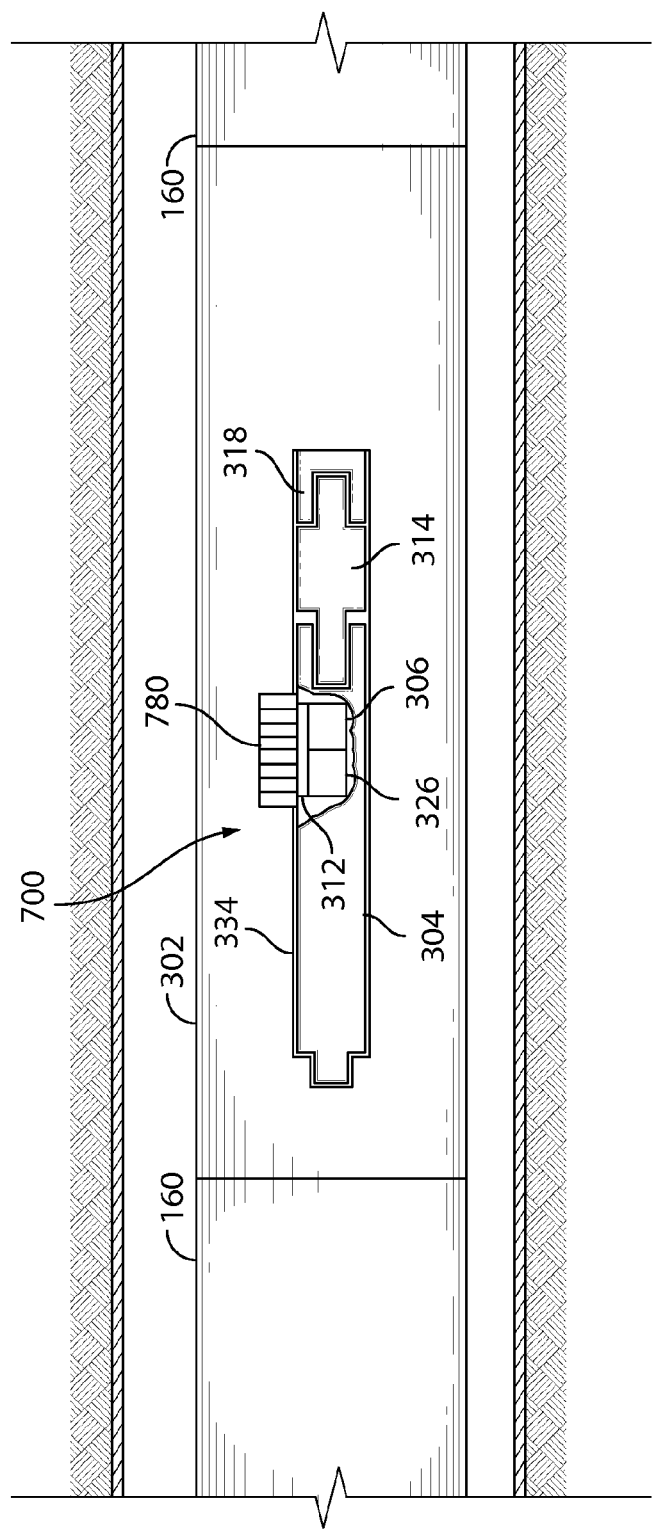
FIG. 7 is a plan view of at least a portion of an example implementation of the apparatus shown in FIG. 4 according to one or more aspects of the present disclosure.

FIG. 7 is a top view of another implementation of the downhole tool 300 shown in FIGS. 4-6, herein designated by reference numeral 700. The fluid flow 70 depicted in other figures is omitted from FIG. 7 for clarity. The downhole tool 700 shown in FIG. 7 is substantially similar to the downhole tool 300 shown in FIGS. 4-6. However, the downhole tool 700 also comprises a cleaner 780. The cleaner 780 may be or comprise one or more wipers, brushes, and/or other cleaners secured to the body 302 such that the spectrometry sensor 306, the light source 326, and/or the optical window 312 contacts the cleaner 780 each time the sensor member 304 is deployed and/or retracted. Accordingly, contaminants and/or other materials fouling the spectrometry sensor 306, the light source 326, and/or the optical window 312 may be at least partially removed each time the sensor member 304 is deployed and/or retracted. However, other means for cleaning the spectrometry sensor 306, the light source 326, and/or the optical window 312 are also within the scope of the present disclosure.

Figure 8:
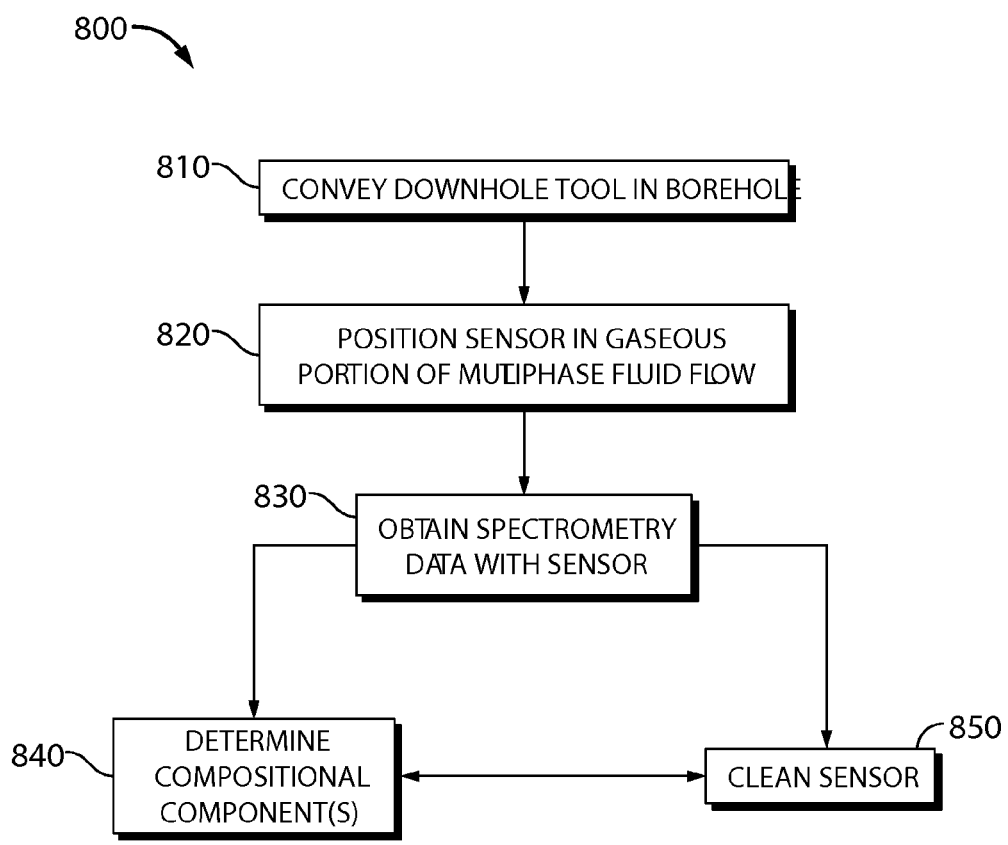
FIG. 8 is a flow-chart diagram of at least a portion of a method according to one or more aspects of the present disclosure.

FIG. 8 is a flow-chart diagram of at least a portion of a method (800) according to one or more aspects of the present disclosure. The method (800) may be performed utilizing the apparatus shown in one or more of FIGS. 1-7 and/or other apparatus implemented according to one or more aspects of the present disclosure.

Referring to FIG. 8 with continued reference to FIGS. 1-7, the method (800) may include conveying (810) a downhole tool within production tubing 20 and/or other tubular structure in a wellbore 10 extending into a subterranean formation 15. The downhole tool may be, comprise, form a portion of, or otherwise have one or more aspects in common with the downhole tool 100 shown in FIGS. 1 and 2, the downhole tool 300 shown in FIGS. 4-6, the downhole tool 700 shown in FIG. 7, and/or other downhole tools within the scope of the present disclosure.

After such conveyance, a spectrometry sensor of the downhole tool may be positioned (820) in a gaseous portion of a multiphase fluid flowing within the tubular structure, such as by rotating and/or otherwise extending a member carrying the sensor away from a body of the tool. The spectrometry sensor may be, comprise, form a portion of, or otherwise have one or more aspects in common with the sensor 130 shown in FIGS. 1-3, the sensor 306 shown in FIGS. 4-7, and/or other sensors within the scope of the present disclosure. The member carrying the sensor may be substantially similar to the sensor member 120 shown in FIGS. 1 and 2, the sensor member 304 shown in FIGS. 4-7, and/or other sensor positioning means within the scope of the present disclosure.

Positioning (820) the spectrometry sensor in the gaseous portion of the multiphase fluid may entail moving the sensor in the wellbore in a direction having a component opposite the direction of gravity. For example, the sensor may be rotated and/or otherwise extended from a body of the downhole tool into contact with the production tubing, and such rotation may cause the body of the downhole tool to settle at or near the bottom of the wellbore in response to gravitational forces, as the downhole tool body may have a mass and, thus, a rotational moment that are substantially greater than a corresponding mass and rotational moment of the sensor and sensor positioning means.

The method (800) may also include utilizing the spectrometry sensor to obtain (830) spectrometry data associated with the multiphase fluid. For example, utilizing the spectrometry sensor to obtain spectrometry data associated with the multiphase fluid may include operating a light source of the downhole tool to direct photons into the multiphase fluid, and detecting photons reflected from the multiphase fluid. The light source may be substantially similar to the light source 180 shown in FIGS. 1-3, the light source 326 shown in FIGS. 4-7, and/or others within the scope of the present disclosure. The sensor positioning means may carry the light source adjacent or proximate the spectrometry sensor. The light source may instead be disposed internal to the downhole tool and operable to transmit light energy to a measurement region associated with the sensor, such as via one or more optical conductors.

The method (800) may also include determining (840) one or more compositional components of the gaseous portion of the multiphase fluid based on the obtained spectrometry data. Such determination (840) may be via one or more known and/or future-developed methods, and may utilize an electronics module of the downhole tool that is operable to determine the compositional component(s) based on the obtained spectrometry data. The electronics module may have one or more aspects in common with the electronics module 140 shown in FIGS. 1-3, the electronics module 310 shown in FIGS. 4 and 6, and/or others within the scope of the present disclosure. Such determination (840) may also or instead utilize surface equipment disposed at a surface from which the wellbore originates, in which case the method (800) may also include transmitting the obtained spectrometry data to the surface equipment. The surface equipment may have one or more aspects in common with the surface equipment 60 shown in FIG. 1, among others within the scope of the present disclosure.

The method (800) may also comprise cleaning (850) the spectrometry sensor with a cleaner coupled with the body. The cleaner may have one or aspects in common with the cleaner 780 shown in FIG. 7, and cleaning the spectrometry sensor may entail contacting the spectrometry sensor with the cleaner by moving the spectrometry sensor past the cleaner.

Figure 9:
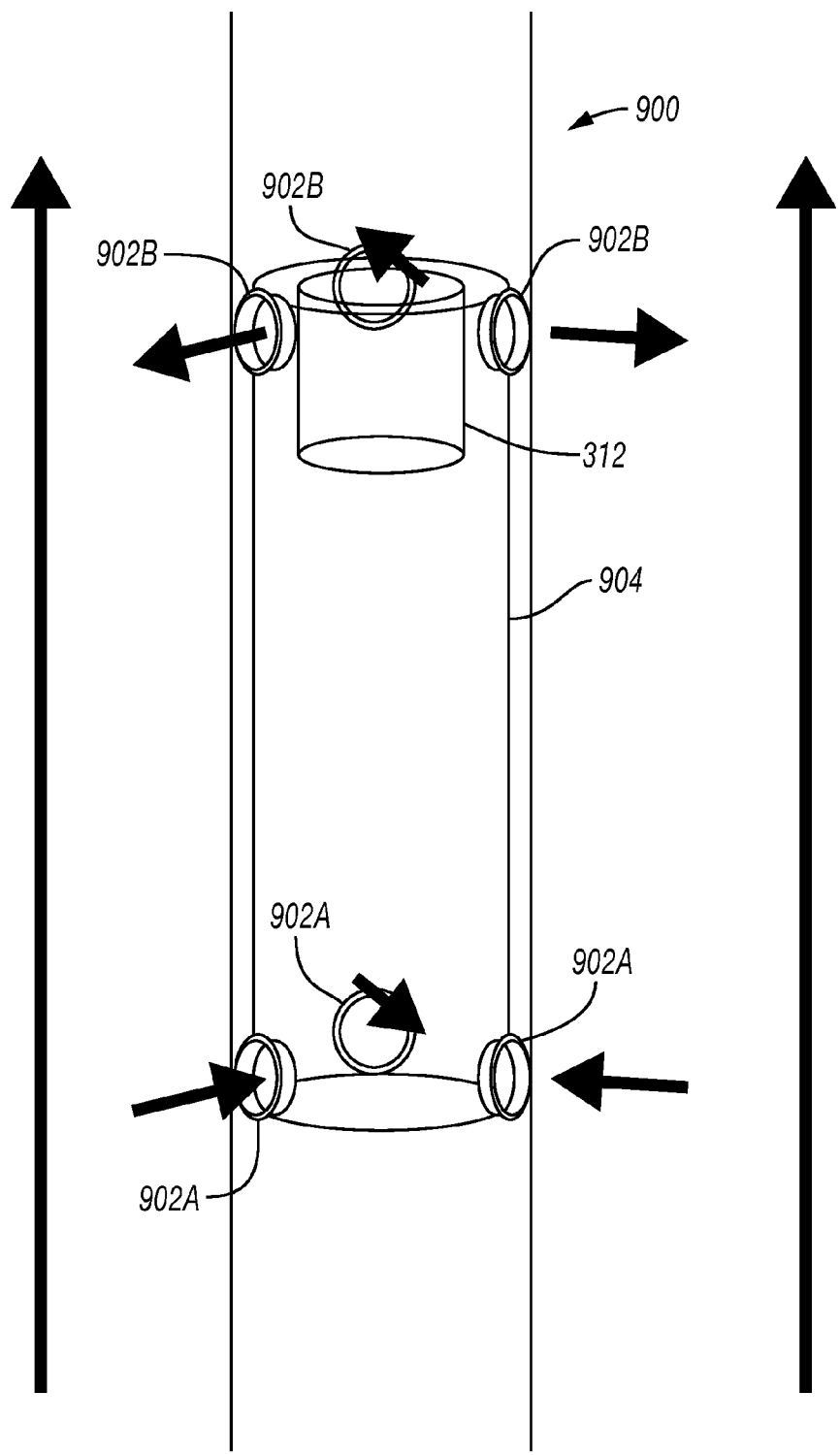
FIG. 9 is a schematic view of an embodiment of a fluid separating component as a sleeve having holes.

Other embodiments of this disclosure involves means of protecting an optical window from contamination, droplets, liquid, or other particles from the borehole fluid which interfere with optical window measurements by separating a substantially dry gas from these particles. The dry gas separated from the borehole fluid may pass over the optical window, while contact between the optical window and interfering particles may be reduced. One or more embodiments involves means of protecting an optical window involves using a protective sheath to protect the window and improve the structural strength of the tool. As illustrated in FIG. 9, and referring back to FIGS. 4-6 collectively, the protective sheath 900 may include holes 902 configured such that liquids may flow through. In some embodiments, combinations of fluids, liquids, or particles may flow in through inlet holes 902a and out through outlet holes 902b. The sheath 900 may be disposed around a downhole tool 300, such that during operation of the downhole tool 300, there may be an annulus between the wellbore and the downhole tool 300, and there may be a cavity 904 between the sheath 900 and the downhole tool 300. The holes 902 may be positioned on the sheath 900 to overlap the ends of the cavity 904.

During operation of the downhole tool 300 and the sheath 900, fluid may flow upwards with respect to the position of the downhole tool 300. A portion of the upwardly flowing fluid may enter the sheath 900 at the inlet holes 902a. The fluid entering the holes 902 may include less particles and/or droplets due to the principle of inertial separation. In some embodiments, the holes 902 may be shaped and/or sized so that the fluid flowing in is separated by inertia, or so that the fluid flowing in comprises less particles and/or droplets than fluid passing the sleeve 900 and not entering the holes 902. The holes 902 may also have outer edges having protruding lips configured to avoid layers of liquid entering the holes 902. The layers of liquid may exist on the outer surface of the downhole tool 300 in the wet gas regime. The lips may also aid in inertial separation of the flow from the holes 902. Further, the fluid entering the holes 902 may also be separated due to gravity, where heavier particles and/or droplets are separated from dry gas. As a result, the fluid exiting through the holes 902b may be predominantly dry gas and may have less particles and/or droplets compared to the fluid entering the holes 902a, and/or the fluid flowing upwards not entering the holes 902.

The optical window 312 of the downhole tool 300 may be offset from the holes 902 so that droplets entering the ports do not flow directly onto the window 312. The cavity 904 may be shaped to have a diameter that is sufficient to reduce the flow velocity of the cavity 904 and a length between the inlet and window that is sufficient to separate the droplets and particles by gravity.

Another embodiment of a system designed to separate borehole fluid or control fluid flow to reduce contamination of flow of projectiles or particles at the optical window 312 involves a downhole tool 300 designed to have a reduced diameter in a region of the inlet holes 902a, such that the local pressure in the annulus may be increased, which may cause an increase in the pressure difference between the inlet and outlet holes. The increased pressure difference may increase the flow rate in the cavity, and the increased velocity may reduce the fluid residence time in front of the window, thereby allowing a higher fluid sample rate or update rate. Moreover, the direction of flow in the cavity may remain constant, and may not be substantially affected by the direction of flow in the main outer annular flow path. As such, the direction of flow in the cavity may be substantially constant and separate from various flow paths in the main outer annular path, such as in variable inclinations and horizontal well configurations.

Figures 10, 11:
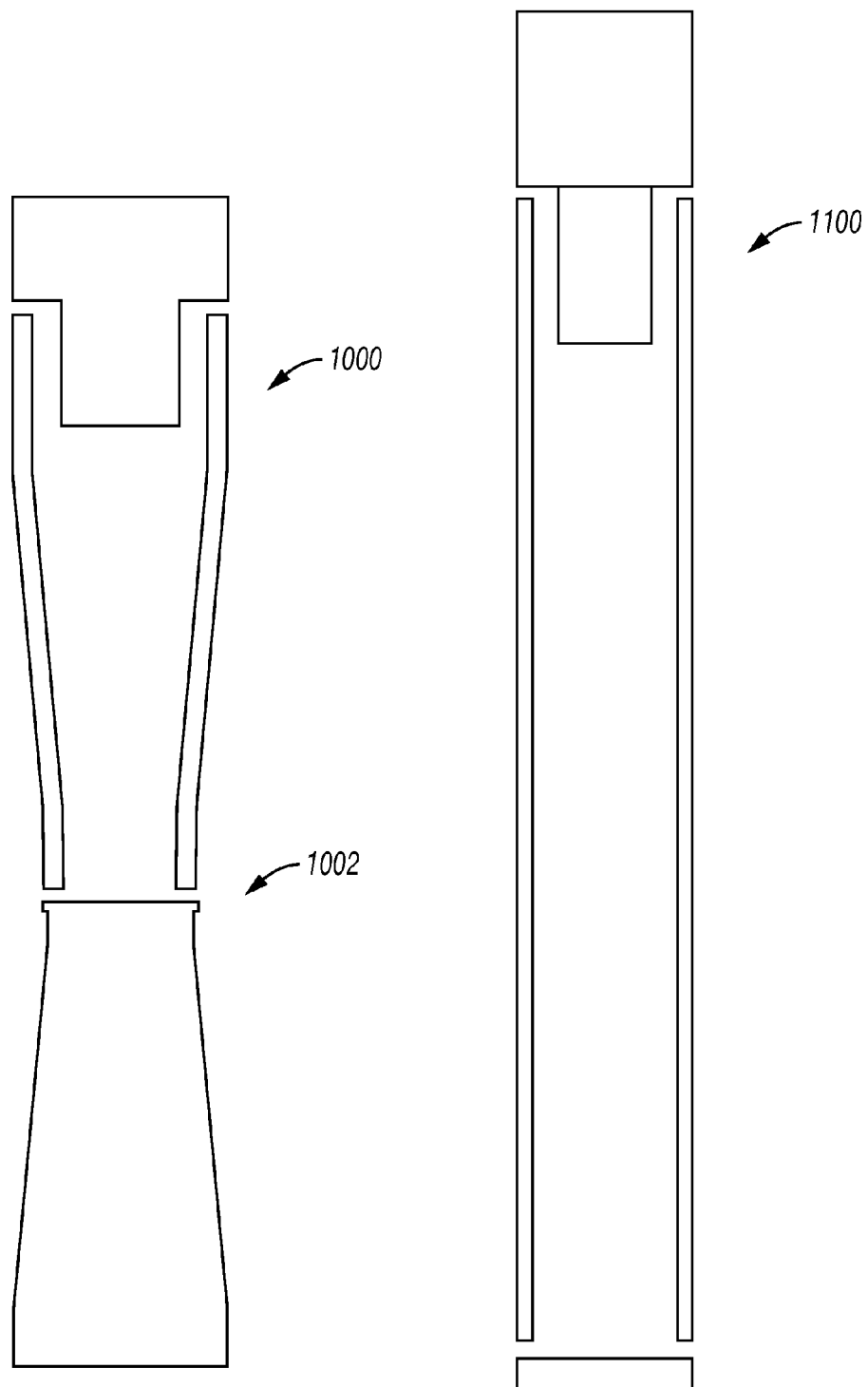
FIG. 10 is an illustration of an embodiment where the tool body has a portion having a smaller diameter.
FIG. 11 is an illustration of an embodiment of a fluid separating component having an elongated cavity.

The increase of pressure difference at the portion of the tool 300 having a reduced diameter increases the flow rate in the cavity may similar to a pump effect. Such a tool shape is represented in the pump-shaped body 1000 of FIG. 10, where the pump-shaped body 1000 may be a portion of the tool 300 having a region 1002 with a reduced diameter.

In another embodiment, the cavity length may be sufficiently long to improve the gravity segregation in the cavity. Furthermore, the increased distance between holes 902 of such an elongated cavity, as illustrated in the elongated body 1100 of FIG. 11, may increase a pressure drop between the inlet and outlet holes 902a and 902b, and may increase the sampling rate.

Figure 12:
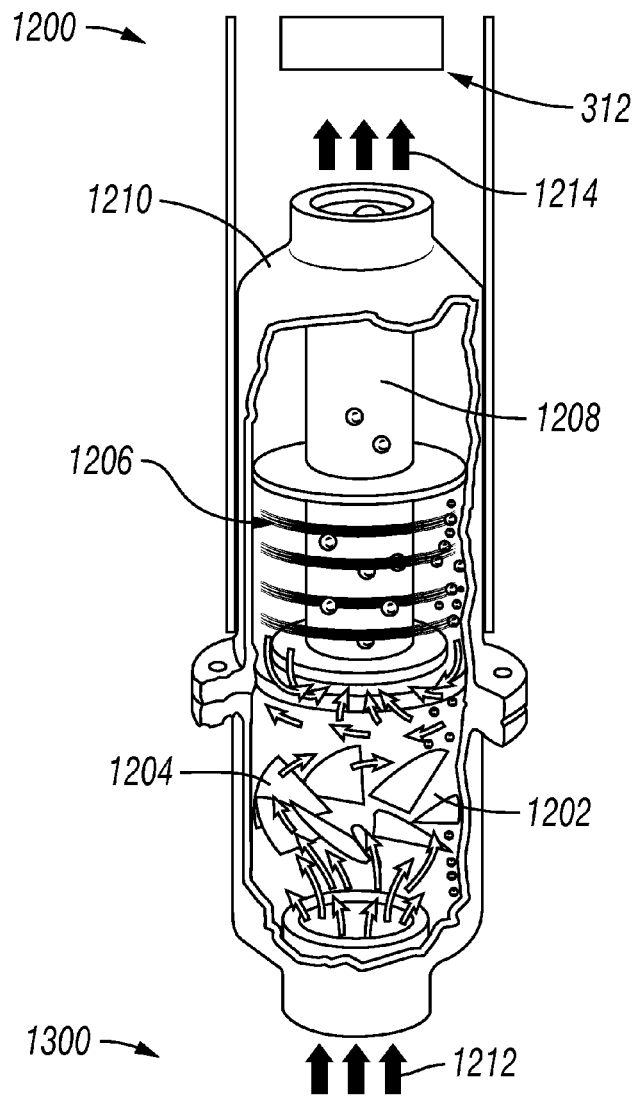
FIG. 12 is a schematic view of an embodiment of a fluid separating component having separator blades.

One or more embodiments may also include curved tube separators, where fluid entering inlet ports may be passed through components which impart centrifugal forces on the entering fluid to separate the droplets, particles, and other components of the entering fluid. As illustrated in FIG. 12, the curved tube separator 1200 may include a centrifugal separator 1202 having one or multiple blades 1204 spinning axially with respect to the length of the separator 1200. The separator 1200 may include a high density component 1206 and a central gas pipe 1208. Substantially dry gas in the fluid may separate from the fluid and may flow through the central gas pipe 1208, while droplets, particles, and other liquids may remain outside the gas pipe in the high density component 1206. The separated dry gas may be analyzed at an optical window 312 with reduced contamination from liquids or other interfering particles or projectiles, while the separated droplets, particles, and other liquids may eventually be drained from the separator 1200 via a drain 1210 or other suitable receptacle or outlet. In one or more embodiments, entering fluid 1212 may be separated through the curved tube separator 1200, such that heavier fluids such as droplets, particles, and other liquids may be separated from drier gases, and the exiting fluid 1214 may be substantially drier than the entering fluid 1212.

Figure 13A:
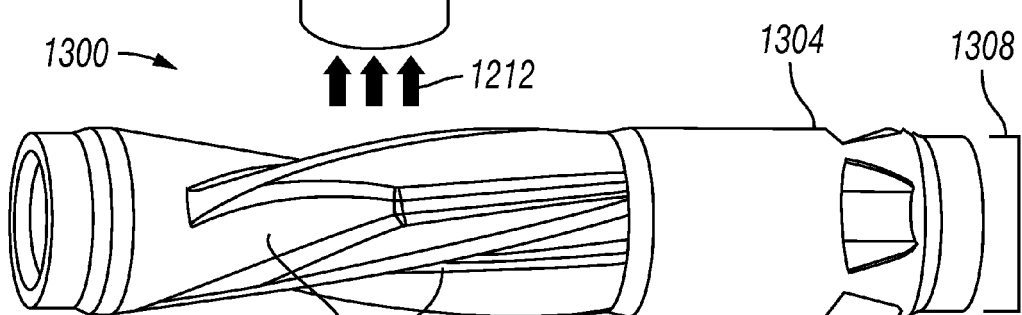
FIGS. 13A and 13B are schematic and cross-sectional views, respectively, of a fluid separating component having curved conduits.
Figure 13B:
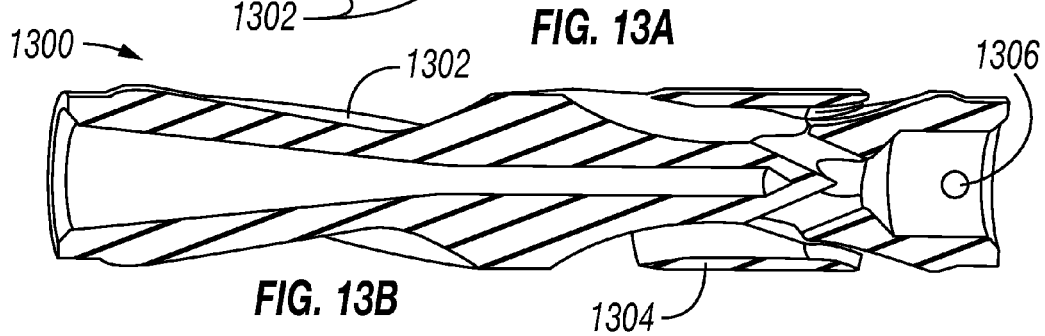

Another embodiment for separating components of borehole fluids to reduce contamination of an optical window 312 of a downhole tool 300 involves a curved channel separator 1300, illustrated schematically and in longitudinal cross-section in FIGS. 13A and 13B, respectively. The tool 300 may include a curved channel separator 1300 configured adjacent to and/or around a window 312. During operation of the downhole tool 300, fluid may pass through the curved conduits 1302 of the curved channel separator 1300, and the rotation of the tool 300 and/or the curved channel separator 1300 may generate centrifugal forces on the flowing fluid. The curved channel separator 1300 may include an outer component 1304 having holes configured so that during operation and/or rotation of the curved channel separator 1300 and/or tool 300, the centrifugal forces on the fluid result in the denser droplets and particles flowing out the holes of the outer component 1304 and away from a cavity 1306 enclosing the spectrometry sensor 306 and/or optical window 312. In some embodiments, the curved channel separator may include baffles, blades, or any other suitable structure configured such that liquid droplets may coalesce on the baffles, rather than on the window 312.

In one or more embodiments, the downhole tool 300 may include an active device, such as a motor 1308, for example, which is connected to the curved channel separator and operates the curved channel separator to centrifuge heavier entities (e.g., droplets, particles, liquids) from the wet gas flow. The active device 1308 may rotate the curved channel separator 1300 at a sufficient speed to centrifuge heavier entities through the curved channel separator.

Figure 14:
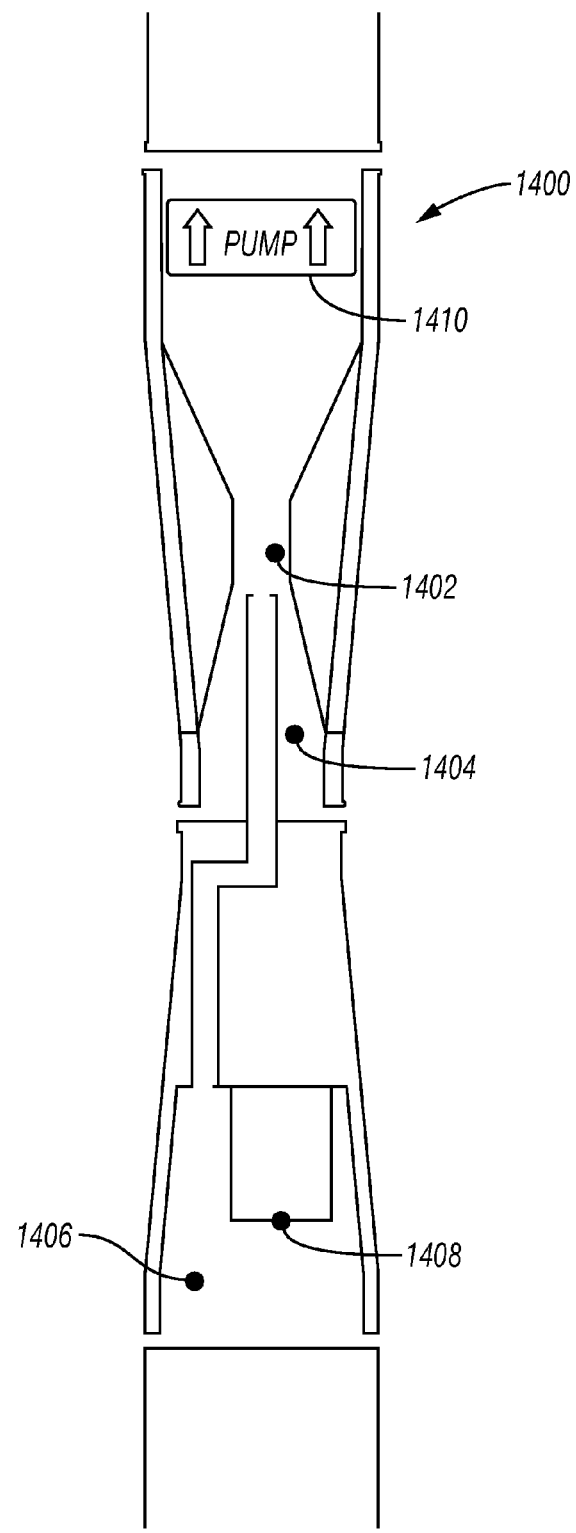
FIG. 14 is an embodiment of a fluid separating component having a multiple flow paths and a pump.

In some embodiments, the downhole tool 300 may include a jet pump component 1400, as illustrated in FIG. 14. The jet pump component 1400 may include a primary flow path 1404 and a secondary flow 1406 path. The secondary flow path may be connected to or may be an outlet from a dry chamber 1408, and the window 312 may be positioned in the dry chamber 1408. The jet pump component 1400, or a separately powered pump, may control the velocity or flow of fluid (e.g., wet gas) up through the jet pump component. The downhole conditions and geometrical configuration of the jet pump component 1400 may control the flow of fluid through a cavity of the window 312. In some embodiments, the jet flow component 1400 may include a jet pump 1402 which causes a pressure drop in the jet pump component 1402. The configuration of the primary flow path 1404 and secondary flow path 1406 may be such that fluid through the primary flow path 1404 entrains fluid from the secondary flow path 1406. By adjusting the flow rate of fluid from the secondary flow path 1406 to the primary flow path 1404 to a value low enough to maintain gravitational separation in the cavity 1406, the flow of fluid may be controlled through the fluid separator, and the gas near the window 312 may be drier.

Embodiments of the disclosure include fluid separating components having a combination of the components described above. For example, a fluid separating component may include a sleeve 900 with holes 902 and an elongated cavity 1100 designed for gravitational separation of fluids. Furthermore, in addition to inertial fluid separation and gravitational fluid separation, the fluid separating component may also include a jet pump component 1400 having flow paths designed to adjust the flow rate of fluid through the fluid separating component. Additionally, embodiments may also include a pump 1410 to further control fluid flow.

In view of the entirety of the present disclosure, a person having ordinary skill in the art should readily recognize that the present disclosure introduces an apparatus comprising: a downhole tool conveyable within a tubular within a wellbore extending into a subterranean formation, wherein the downhole tool comprises: a body; a member having a first end and a second end, wherein the first end is rotatably coupled to the body; and a spectrometry sensor disposed proximate the second end of the member.

The member may be a first member and the downhole tool may further comprise a second member having a first end rotatably coupled to the body and a second end rotatably coupled to the second end of the first member.

A rotational axis about which the member rotates relative to the body may be substantially perpendicular to a longitudinal axis of the body. Rotation of the member relative to the body may be within a plane that is at least partially defined by the longitudinal axis of the body. The rotational axis may be a first rotational axis, and a second rotational axis about which the member also rotates may be substantially coincident with the longitudinal axis of the body. The member may rotate around the second rotational axis relative to the body.

The downhole tool may further comprise a light source generating photons detectable by the spectrometry sensor after interaction with a fluid adjacent the spectrometry sensor. The light source may be disposed proximate the second end of the member. The light source may be disposed within the body, in which case the downhole tool may further comprise: an optical window disposed proximate the second end of the member; and an optical conductor transmitting light from the light source to the optical window. The optical window may substantially comprise sapphire. The fluid may be a moving fluid, and a normal vector extending from an external surface of the optical window or the spectrometry sensor may be angularly offset from a flow direction of the moving fluid by not more than about ninety degrees. The external surface of the optical window may otherwise substantially non-parallel with a flow direction of the moving fluid. The light source may comprise a capacitor bank and a flash lamp.

The light source may transmit photons to a measurement region located in the fluid adjacent the spectrometry sensor. A volume of the measurement region may be less than about five cubic millimeters. The volume may be about one cubic millimeter.

The member may be disposed at least partially within a recess in an exterior profile of the body when the member is not rotated away from the body. The member may not protrude from the recess when not rotated away from the body. The member may be fully enveloped within the recess when not rotated away from the body. The member may be substantially flush and/or level with an outer surface of the body when not rotated away from the body.

A sampling rate of the spectrometry sensor may be less than about five Hz. The sampling rate may be about one Hz.

The spectrometry sensor may comprise a plurality of sensor channels each operable to detect photons within a respective range of wavelengths. The plurality of sensor channels may each correspond to a compositional component of a fluid flowing past the downhole tool within the tubular. The spectrometry sensor may comprise a six-channel spectrometry sensor.

The apparatus may further comprise first and second swiveling mechanisms disposed on opposite ends of the downhole tool.

The downhole tool may further comprise an actuator disposed in the body and operably connected to impart motion to the first end of the member. The actuator may comprise a motor operable to impart rotational motion to the member. The member may be a first member, and the downhole tool may further comprise: a threaded feature; and a second member having a first end rotatably coupled to the body and a second end rotatably coupled to the second end of the first member. The actuator may comprise a motor operable to impart rotational motion to the threaded feature. At least one of the first end of the first member and the first end of the second member may be threadedly coupled to the threaded feature such that rotation of the threaded feature imparted by the motor imparts linear motion of the first end of the first member relative to the first end of the second member.

The downhole tool may further comprise an electronics module electrically connected to the spectrometry sensor by one or more electrical conductors, and the apparatus may further comprise a telemetry module electrically connected to the electronics module by one or more electrical conductors. The downhole tool may be a wireline tool electrically connected to surface equipment by a wireline cable.

The downhole tool may further comprise a cleaner coupled with the body proximate the spectrometry sensor when the member is not rotated away from the body. The cleaner may contact the spectrometry sensor when rotation of the member moves the spectrometry sensor past the cleaner. The cleaner may comprise a brush and/or a wiper.

The present disclosure also introduces an apparatus comprising: a downhole tool conveyable within a tubular within a wellbore extending into a subterranean formation, wherein the downhole tool comprises: a body; an optical sensor operable in the detection of a compositional component of a fluid in the tubular; and a member operable to position the optical sensor away from the body.

The member may be operable to position the optical sensor by rotating away from the body.

The apparatus may further comprise an actuator operable to impart rotary motion to the member. The actuator may be further operable to: rotate the member out of a recessed portion of an exterior profile of the body; and rotate the member into the recessed portion of the exterior profile of the body.

The member may be a first member, the downhole tool may further comprise a second member, and the first and second members may be collectively operable to cooperatively position the optical sensor away from the body.

The downhole tool may further comprise a light source generating photons detectable by the optical sensor after interaction with a fluid adjacent the optical sensor. The optical sensor may comprise an optically transparent window. The downhole tool may further comprise an optical conductor transmitting light from the light source to the optically transparent window.

The apparatus may further comprise a plurality of swiveling mechanisms permitting rotation of the downhole tool relative to the tubular.

The downhole tool may further comprise a cleaner operable to clean the optical sensor. The cleaner may be operable to clean the optical sensor as the member moves the optical sensor past the cleaner. The cleaner may be disposed in a recess in an exterior profile of the body, and the cleaner may be operable to clean the optical sensor as the member moves in and out of the recess.

The present disclosure also introduces a method comprising: conveying a downhole tool within tubular within a wellbore extending into a subterranean formation, wherein the downhole tool comprises: a body; a member having a first end rotatably coupled to the body; and a spectrometry sensor disposed proximate a second end of the member; and positioning the spectrometry sensor in a gaseous portion of a multiphase fluid flowing within the tubular by rotating the member away from the body.

The method may further comprise utilizing the spectrometry sensor to obtain spectrometry data associated with the multiphase fluid. Utilizing the spectrometry sensor to obtain spectrometry data associated with the multiphase fluid may comprise: operating a light source of the downhole tool to direct photons into the multiphase fluid; and detecting photons reflected from the multiphase fluid. The method may further comprise determining a compositional component of the gaseous portion of the multiphase fluid based on the obtained spectrometry data. Determining the compositional component may utilize an electronics module of the downhole tool operable to determine the compositional component based on the obtained spectrometry data. Determining the compositional component may utilize surface equipment disposed at a surface from which the wellbore originates, and the method may further comprise transmitting the obtained spectrometry data to the surface equipment.

Positioning the spectrometry sensor in the gaseous portion of the multiphase fluid may comprise moving the sensor in the wellbore in a direction having a component opposite the direction of gravity.

Rotating the member away from the body may impart rotational motion to the body relative to the tubular.

The method may further comprise cleaning the spectrometry sensor with a cleaner coupled with the body. Cleaning the spectrometry sensor may comprise contacting the spectrometry sensor with a cleaner by moving the member relative to the cleaner.

Rotating the member away from the body may comprise operating an actuator of the downhole tool to impart rotary motion to the member.

The method may further comprise retracting the spectrometry sensor from the gaseous portion of the multiphase fluid.

The disclosure also introduces an apparatus comprising a downhole tool conveyable within a tubular within a wellbore extending into a subterranean formation, wherein the downhole tool comprises a body, a spectrometry sensor coupled to the body, a spectrometry window configured to substantially cover the spectrometry sensor from an outside of the downhole tool, and a fluid separating component configured about the body, wherein the fluid separating component is shaped such that a heavier fluid from a fluid flow along the downhole tool is drawn away from the spectrometry window, wherein the heavier fluid comprises fluid droplets, particles, liquids, or combinations thereof.

In some embodiments, the fluid separating component comprises a sleeve comprising a plurality of holes, wherein the sleeve is positioned about the spectrometry window, and wherein the holes are positioned such that fluid flowing in a first hole of the plurality of holes and out of the sleeve from a second hole in the plurality of holes comprises less heavier fluid than other fluid flowing in the wellbore. The fluid flowing past the spectrometry window may be drier gas than the other fluid flowing in the wellbore. In some embodiments, a portion of the body in the sleeve comprises a smaller diameter than a standard diameter of the body, wherein the smaller diameter of the body results in an increase in local pressure in an annulus between the fluid separating component and the body.

In some embodiments, the fluid separating component is configured to rotate, and wherein the fluid separating component comprises curved channels configured such that heavier fluid coalesce through and out the curved channels when the fluid separating component rotates. The downhole tool may also comprise an active device configured to rotate the fluid separating component.

The disclosure also introduces an apparatus where the fluid separating component comprises a primary flow path and a secondary flow path, wherein the spectrometry window is disposed in a chamber connected to the secondary flow path, and wherein the fluid separating component is configured such that during operation of the fluid separating component, heavier fluid flows from the secondary flow path to the primary flow path and away from the spectrometry window. Some embodiments include a jet pump coupled to the fluid separating component, wherein the jet pump is configured to draw heavier fluids from the secondary flow path to the primary flow path and away from the spectroscopy window.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same goals and/or achieving the same benefits of the example implementations introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. §1.72(b) to permit the reader to quickly ascertain the nature of the technical disclosure. It is submitted with the understanding that it will not be used to interpret or limit the scope or meaning of the claims.

What is claimed is:

1. A method, comprising:
   conveying a downhole tool within tubular within a wellbore extending into a subterranean formation, wherein the downhole tool comprises:
   a body;
   a member having a first end rotatably coupled to the body; and
   a spectrometry sensor disposed proximate a second end of the member;
   positioning the spectrometry sensor in a gaseous portion of a multiphase fluid flowing within the tubular by rotating the member away from the body, out of a recess formed in an exterior profile of the body; and
   cleaning the spectrometry sensor by contacting the spectrometry sensor with a cleaner, disposed in the recess, when rotation of the member moves the spectrometry sensor past the cleaner and wiping or brushing the spectrometry sensor with the cleaner by rotating the member out of the recess such that the spectrometry sensor is moved across the cleaner.

2. The method of claim 1 further comprising utilizing the spectrometry sensor to obtain spectrometry data associated with the multiphase fluid.

3. The method of claim 2 wherein utilizing the spectrometry sensor to obtain spectrometry data associated with the multiphase fluid comprises:
   operating a light source of the downhole tool to direct photons into the multiphase fluid; and
   detecting photons reflected from the multiphase fluid.

4. The method of claim 1 wherein positioning the spectrometry sensor in the gaseous portion of the multiphase fluid comprises moving the sensor in the wellbore in a direction having a component opposite the direction of gravity.

5. The method of claim 1 wherein rotating the member away from the body imparts rotational motion to the body relative to the tubular.

6. The method of claim 1 further comprising generating photons detectable by the spectrometry sensor after interaction with the gaseous portion of the multiphase fluid adjacent the spectrometry sensor.

7. The method of claim 1 wherein the cleaner comprises a brush and/or a wiper.

8. The method of claim 1 further comprising cleaning the spectrometry sensor by wiping or brushing the spectrometry sensor with the cleaner by rotating the member into the recess such that the spectrometry sensor is again moved across the cleaner.

9. The method of claim 1 wherein positioning the spectrometry sensor orients a normal vector extending from an external sensing surface of the spectrometry sensor to be angularly offset from a flow direction of the multiphase fluid by not more than about ninety degrees.

10. The method of claim 1 wherein the downhole tool further comprises:
   a light source generating photons detectable by the spectrometry sensor after the photons interact with the gaseous portion of the multiphase fluid adjacent the spectrometry sensor; and
   an optical window disposed proximate the second end of the member, wherein the photons generated by the light source and detected by the spectrometry sensor pass through the optical window, and wherein positioning the spectrometry sensor orients a normal vector extending from an external surface of the optical window to be angularly offset from a flow direction of the multiphase fluid by not more than about ninety degrees.

11. The method of claim 1 wherein the spectrometry sensor comprises a plurality of sensor channels each operable to detect photons within a respective range of wavelengths, wherein the plurality of sensor channels each correspond to one of a plurality of compositional components of the gaseous portion of the multiphase fluid, and wherein the method further comprises obtaining spectrometry data corresponding to at least one of the plurality of compositional components utilizing the spectrometry sensor positioned in the gaseous portion of the multiphase fluid.

12. The method of claim 11 further comprising obtaining spectrometry data corresponding to more than one of the plurality of compositional components utilizing the spectrometry sensor positioned in the gaseous portion of the multiphase fluid.

13. The method of claim 1 further comprising utilizing the spectrometry sensor to obtain spectrometry data associated with the gaseous portion of the multiphase fluid at a sampling rate of about one hertz.

14. An apparatus, comprising:
a downhole tool conveyable within a tubular within a wellbore extending into a subterranean formation, wherein the downhole tool comprises:
a body;
a spectrometry sensor coupled to the body,
a spectrometry window configured to substantially cover the spectrometry sensor from an outside of the downhole tool; and
a fluid separating component configured about the body, wherein the fluid separating component is shaped such that a heavier fluid from a fluid flow along the downhole tool is drawn away from the spectrometry window, wherein the heavier fluid comprises fluid droplets, particles, liquids, or combinations thereof, wherein the fluid separating component comprises a sleeve comprising a plurality of holes, wherein the sleeve is positioned about the spectrometry window, and wherein the holes are positioned such that fluid flowing in a first hole of the plurality of holes and out of the sleeve from a second hole in the plurality of holes comprises less heavier fluid than other fluid flowing in the wellbore.

15. The apparatus of claim 14 wherein a portion of the body in the sleeve comprises a smaller diameter than a standard diameter of the body, wherein the smaller diameter of the body results in an increase in local pressure in an annulus between the fluid separating component and the body.

16. A method, comprising:
conveying a downhole tool within tubular within a wellbore extending into a subterranean formation, wherein the downhole tool comprises:
a body;
a member having a first end rotatably coupled to the body; and
a spectrometry sensor disposed proximate a second end of the member; and
positioning the spectrometry sensor in a gaseous portion of a multiphase fluid flowing within the tubular by rotating the member away from the body, wherein positioning the spectrometry sensor orients a normal vector extending from an external sensing surface of the spectrometry sensor to be angularly offset from a flow direction of the multiphase fluid by not more than about ninety degrees;
rotating the member away from the body includes rotating the member out of a recess formed in an exterior profile of the body;
the downhole tool further comprises a cleaner disposed in the recess; and
the method further comprises cleaning the spectrometry sensor by rotating the member out of or into the recess to thereby swipe the spectrometry sensor across the cleaner.

17. The method of claim 16 wherein the spectrometry sensor comprises a plurality of sensor channels each operable to detect photons within a respective range of wavelengths, wherein the plurality of sensor channels each correspond to one of a plurality of compositional components of the gaseous portion of the multiphase fluid, and wherein the method further comprises obtaining spectrometry data corresponding to more than one of the plurality of compositional components utilizing the spectrometry sensor positioned in the gaseous portion of the multiphase fluid.

18. The method of claim 16 wherein the cleaner comprises a brush and/or a wiper.

* * * * *